United States Patent
Traverso et al.

(10) Patent No.: US 11,833,065 B2
(45) Date of Patent: Dec. 5, 2023

(54) ARTIFICIAL WRIST

(71) Applicants: FONDAZIONE ISTITUTO ITALIANO DI TECNOLOGIA, Genoa (IT); INAIL—ISTITUTO NAZIONALE PER L'ASSICURAZIONE CONTRO GLI INFORTUNI, Rome (IT)

(72) Inventors: Simone Traverso, Genoa (IT); Andrea Lince, Fresonara (IT); Matteo Laffranchi, Genoa (IT); Lorenzo De Michieli, Genoa (IT)

(73) Assignees: FONDAZIONE ISTITUTO ITALIANO DI TECNOLOGIA, Genoa (IT); INAIL—ISTITUTO NAZIONALE PER L'ASSICURAZIONE CONTRO GLI INFORTUNI, Rome (IT)

( * ) Notice: Subject to any disclaimer, the term of this patent is extended or adjusted under 35 U.S.C. 154(b) by 227 days.

(21) Appl. No.: 17/422,806

(22) PCT Filed: Mar. 18, 2019

(86) PCT No.: PCT/IB2019/052172
§ 371 (c)(1),
(2) Date: Jul. 14, 2021

(87) PCT Pub. No.: WO2019/186319
PCT Pub. Date: Oct. 3, 2019

(65) Prior Publication Data
US 2022/0125605 A1 Apr. 28, 2022

(30) Foreign Application Priority Data
Mar. 26, 2018 (IT) .......................... 102018000003961

(51) Int. Cl.
*A61F 2/58* (2006.01)
*A61F 2/50* (2006.01)
*A61F 2/68* (2006.01)

(52) U.S. Cl.
CPC ...... *A61F 2/585* (2013.01); *A61F 2002/5003* (2013.01); *A61F 2002/5038* (2013.01); *A61F 2002/6854* (2013.01)

(58) Field of Classification Search
CPC .............. A61F 2/585; A61F 2002/6854; A61F 2002/5038; A61F 2/583; A61F 2002/5003; A61F 2/54; A61F 2/543; A61F 2/58
See application file for complete search history.

(56) References Cited

U.S. PATENT DOCUMENTS

| | | | | |
|---|---|---|---|---|
| 4,685,929 A | * | 8/1987 | Monestier | A61F 2/583<br>623/64 |
| 6,896,704 B1 | * | 5/2005 | Higuchi | A61F 2/70<br>623/64 |

(Continued)

FOREIGN PATENT DOCUMENTS

DE 307338 C 6/1916

OTHER PUBLICATIONS

The International Search Report and Written Opinion, dated Jul. 5, 2019.

*Primary Examiner* — Keri J Nelson
*Assistant Examiner* — Cassidy N Stuhlsatz
(74) *Attorney, Agent, or Firm* — Vorys, Sater, Seymour and Pease LLP

(57) ABSTRACT

An artificial wrist including a static body adapted to be bound to a support; a movable body adapted to be bound to an end effector; and a junction block defining an axis of rotation between the static body and the movable body and including a cable suitable to be moved by mutual rotation of (Continued)

the bodies and around the axis of rotation, and elastic member placing the cable under tensile stress and working in opposition to the movement of the cable to define a rest position in which the cable and the elastic member exerts a zero resulting torque on the bodies and, and an activation position in which they exert a non-zero resulting torque on the bodies and, bringing the bodies and back to the rest position.

6 Claims, 3 Drawing Sheets

(56) References Cited

U.S. PATENT DOCUMENTS

| | | | |
|---|---|---|---|
| 7,048,768 B1* | 5/2006 | Rouse | A61F 2/585 |
| | | | 623/61 |
| 7,914,587 B2 | 3/2011 | Archer et al. | |
| 2007/0173955 A1* | 7/2007 | Archer | A61F 2/585 |
| | | | 623/61 |
| 2007/0213842 A1* | 9/2007 | Simmons | A61F 2/68 |
| | | | 623/64 |
| 2017/0007425 A1* | 1/2017 | Veatch | A61F 2/583 |
| 2017/0281368 A1* | 10/2017 | Gill | A61F 2/585 |
| 2018/0064563 A1* | 3/2018 | Gill | A61F 2/586 |

* cited by examiner

ARTIFICIAL WRIST

The present invention relates to an artificial wrist of the type specified in the preamble of the first claim.

In particular, the invention is suitable to be used to connect an end effector (preferably a robotic hand or other prosthetic device) to a support (such as a suitably prosthetic robotic arm), thereby allowing reciprocal movement of the end effector and the support. In detail, the artificial wrist is suitable for use in the industrial or preferably prosthetic field.

Artificial wrists for the manipulation of prosthetic limbs are currently known and used to couple a prosthetic device (usually a prosthetic hand) to a robotic/human limb or a residual limb of the user, thus allowing the prosthetic device to rotate relative to the support.

Briefly, known artificial wrists provide a base element bound to the support, an element which moves relative to the base element and binds to the prosthetic device; and a hinge defining an axis of rotation between the elements and therefore between the support and the device.

An example of an artificial wrist is described in U.S. Pat. No. 7,914,587.

In this artificial wrist the hinge consists of a cross-shaped body interposed between the base element and the movable element and provided with two pairs of arms perpendicular to each other and defining two axes of rotation for said elements; torsion springs, one for each arm, having one end integral with the base element and the other with the movable element, so as to oppose their reciprocal rotation.

A second example of an artificial wrist is described in US2017/0281368.

The hinge of this wrist consists of a pin hinging the elements, a rack engaging the pinion so that rotation of the pinion causes translation of the rack, and springs between the rack and the base element working in opposition to the translation of the rack.

The described prior art has a few major drawbacks.

In fact, artificial wrists are equipped with complex mechanics that are difficult to achieve considering the small dimensions required by artificial wrists.

Another drawback is that artificial wrists (especially if they are prosthetic) require limited dimensions and weights to make their use practical and comfortable, but, as can be easily understood from the examples given above, they have a multiplicity of elements which impose considerable weight and large dimensions.

These drawbacks result in poor comfort of use of artificial prosthetic wrists and high manufacturing costs.

In this context, the technical task underlying the present invention is to devise an artificial wrist, which is capable of substantially obviating at least some of the above-mentioned drawbacks.

Within the scope of said technical task, a major object of the invention is to obtain a low-weight and small-sized artificial wrist.

Another major object of the invention is to provide an artificial wrist, which is low-cost and above all practical and comfortable to use.

The technical task and the specified objects are achieved by means of an artificial wrist as claimed in appended claim 1. Exemplary preferred embodiments are described in the dependent claims.

The features and advantages of the invention will be clarified in the following detailed description of preferred embodiments of the invention, with reference to the accompanying drawings, in which.

Figure 1:
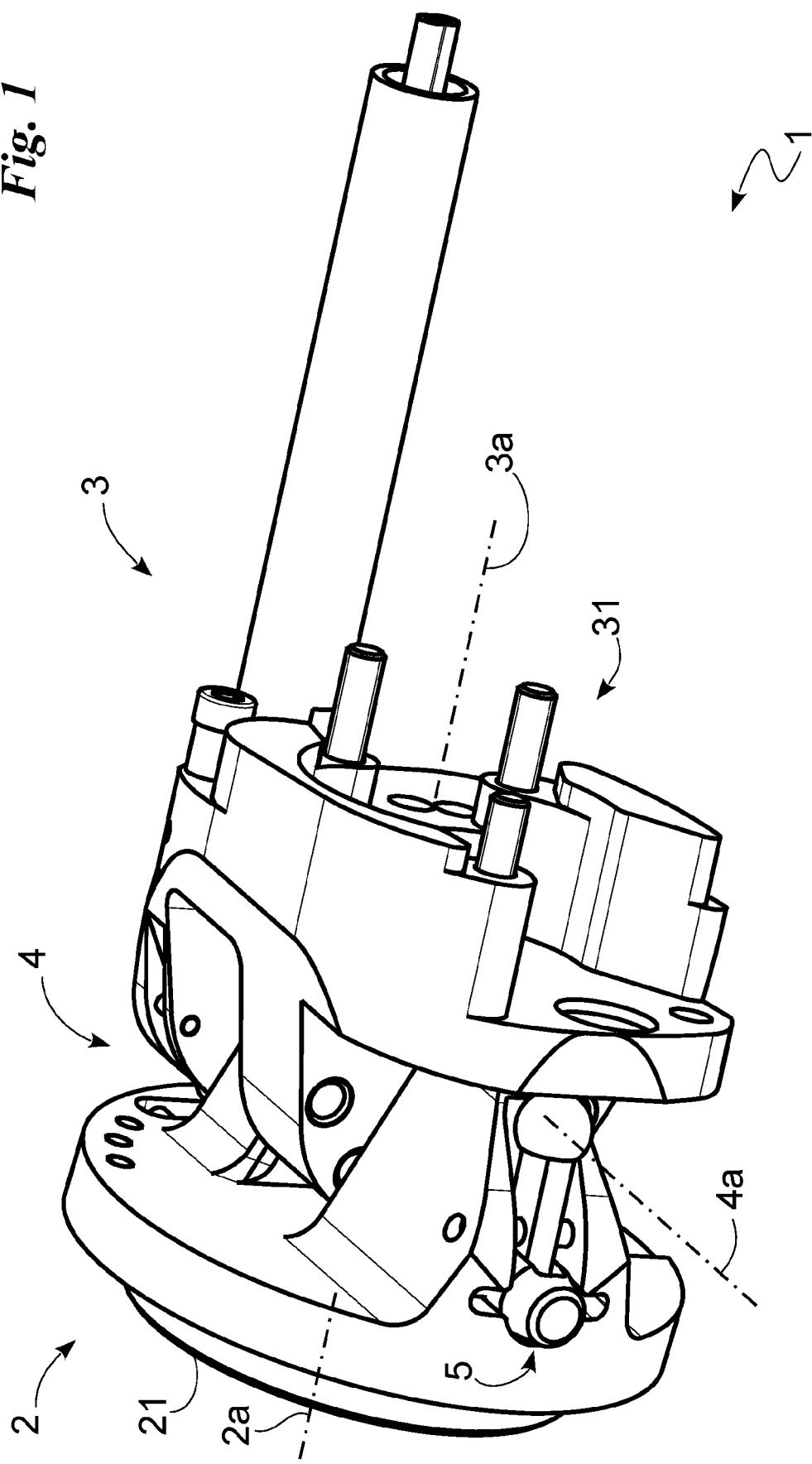
FIG. 1 is a scale representation of an artificial wrist according to the invention.

Herein, the measures, values, shapes and geometric references (such as perpendicularity and parallelism), when used with words like "about" or other similar terms such as "approximately" or "substantially", are to be understood as except for measurement errors or inaccuracies due to production and/or manufacturing errors and, above all, except for a slight divergence from the value, measure, shape or geometric reference with which it is associated. For example, these terms, if associated with a value, preferably indicate a divergence of not more than 10% from said value.

Furthermore, when used, terms such as "first", "second", "higher", "lower", "main" and "secondary" do not necessarily identify an order, a priority relationship or a relative position, but can simply be used to distinguish more clearly the different components from each other.

Unless otherwise indicated, the measurements and data provided in this document are to be considered using International Standard Atmosphere ICAO (ISO 2533).

With reference to the Figures, the artificial wrist according to the invention is indicated as a whole by the number 1.

It is suitable to be used to connect an end effector to a support, allowing at least one rotation between the end effector and the support.

The end effector is preferably a prosthetic device, and specifically a robotic hand.

The support is identifiable as a suitably prosthetic robotic arm or an amputated limb.

The artificial wrist 1 comprises a static body 2 adapted to be bound to a support; a movable body 3 adapted to be bound to an end effector; and at least one junction block 4 between the static body 2 and the movable body 3 and defining an axis of rotation 4a between the static body 2 and the movable body 3.

Preferably, the wrist 1 comprises a single junction block 4 and therefore the bodies 2 and 3 can be moved relative to each other along a single axis of rotation 4a.

The static body 2 defines a first, suitably barycentric longitudinal axis 2a.

The first longitudinal axis 2a is perpendicular to the axis of rotation 4a and appropriately incident to said axis of rotation 4a.

The static body 2 comprises first fastening means 21 for fastening the static body 2 to the support.

The movable body 3 defines a second, suitably barycentric longitudinal axis 3a.

The second longitudinal axis 3a is perpendicular to the axis of rotation 4a and appropriately incident to said axis of rotation 4a.

The movable body 3 comprises second fastening means 31 for fastening the movable body 3 to the end effector.

The fastening means 21 and 31 are known in the art.

The junction block 4 comprises a hinge 41 defining the axis of rotation 4a.

The junction block 4 is suitable to allow and at the same time oppose rotation between the static body 2 and the movable body 3, suitably around the axis of rotation 4a.

It defines, for the artificial wrist 1, a rest position (FIGS. 1-2) in which the resulting torque on the bodies 2 and 3 is zero and therefore the bodies 2 and 3 remain stationary relative to each other; and at least one activation position (FIG. 3) in which the resulting torque on the bodies 2 and 3 is non-zero, causing mutual rotation of the bodies 2 and 3. More specifically, in the activation position, mutual rotation of the bodies 2 and 3 results in a torque acting on the bodies 2 and 3, which is opposite to that generating said mutual rotation and such as to bring the bodies 2 and 3 back to the rest position.

In the rest configuration, the longitudinal axes 2a and 3a are substantially parallel to each other, and specifically one is the continuation of the other.

In the one or more activation configurations, the longitudinal axes 2a and 3a are inclined to each other.

The junction block 4 comprises at least one cable 42 bound to the static body 2 and the movable body 3; and elastic means 43 placing the cable 42 under tensile stress.

Preferably, the junction block 4 comprises two cables 42, of which a first cable 42 is adapted to be tensioned by mutual rotation of the bodies 2 and 3 in a first direction of rotation, and a second cable 42 is adapted to be tensioned by mutual rotation of the bodies 2 and 3 in a second direction opposite to the first direction of rotation.

The action of the cable 42 and the means 43 defines the aforesaid resulting torque.

Each cable 42 has one end bound to the static body 2, preferably in an integral manner. The cables 42 are anchored to the static body 2 on opposite sides with respect to the axis of rotation 4a, and specifically to the first longitudinal axis 2a.

Each cable 42 has the other end bound to the movable body 3, suitably in a non-integral manner as hereinafter better described.

The cable 42 is bound to the movable body 3 on the opposite side of the static body 2. For this purpose, the movable body 3 comprises a channel 32 for the passage of the one or more cables 42.

The channel 32 has an axis of extension that can be perpendicular to the axis of rotation 4a. Specifically, the axis of extension of the channel 32 is inclined to the second longitudinal axis 3a. Alternatively, it is substantially parallel to the second axis 3a.

Preferably, the channel 32 comprises a first sector 32a proximal to the static body 2 and a second sector 32b inclined to the first sector and located on the opposite side of the first sector 32a with respect to the static body 2.

The first sector 32a has a first axis of extension substantially inclined to the second longitudinal axis 3a.

The second sector 32b has a second axis of extension substantially parallel to and suitably distinct from the second longitudinal axis 3a.

The elastic means 43 is suitable to store energy during mutual rotation of the bodies 2 and 3 moving away from the rest position. In detail, they work in opposition to the movement of at least one cable 42 (due to an external torque applied to one of the bodies 2 and 3) so as to create a torque on the bodies 2 and 3, which is opposite and such as to bring the artificial wrist 1 back to the rest position.

In the rest position, the forces of the elastic means 43 and of the at least one cable 42 mainly cause two opposite and substantially equal torques, so that the resulting torque is zero and therefore such as to maintain the artificial wrist 1 in the rest position.

In the activation position, the forces of the elastic means 43 and of the at least one cable mainly cause two opposite and substantially different torques, so that the resulting torque is non-zero and therefore such as to bring the artificial wrist 1 back to the rest position.

The elastic means 43 is preloaded so that in the rest position each cable 42 is tensioned.

The elastic means 43 is interposed between the movable body 3 and said at least one cable 42 so that the transition into the activation position causes the cable 42 to move, thus loading the elastic means 43.

They can have one end integral with the movable body 3 and the other end integral with the at least one cable 42 so that mutual rotation of the bodies 2 and 3 moving away from the rest position, which causes the cable 42 to move, loads the elastic means 43.

The elastic means 43 comprises a spring, which is suitably a tension spring or specifically a compression spring. Preferably, the elastic means 43 is a compression spring, and the end thereof that is integral with the at least one cable 42 is located on the opposite side of the static body 2 with respect to the movable body 3.

The elastic means 43 is preferably housed inside the channel 32, which then guides the sliding of said elastic means 43.

In order to integrally bind the end to the at least one cable 42, the junction block 4 may comprise a fastening head 44 for fastening the cable 42 to the means 43.

The junction block 4 may comprise at least one pulley 45 defining a groove for the sliding of the at least one cable 42.

The pulley 45 is placed at the interface area between the bodies 2 and 3.

Preferably, it is bound, and in detail hinged to the movable body 3 so as to intercept the cable 42 before it reaches the channel 32.

Advantageously, the junction block 4 comprises two pulleys 45 alongside each other so that the sliding grooves define a duct inside which the at least one cable 42 slides, substantially without the possibility of coming out sideways.

The junction block 4 may comprise one or more guiding pins 46 to direct the at least one cable 42.

The guiding pins 46 are located along the path of each cable 42 and define surfaces along which the cable 42 slides during rotation, and therefore a change in position of the artificial wrist 1.

They may be bound, suitably in an integral manner, to the static body 2 and/or to the movable body 3.

Finally, the artificial wrist 1 can comprise a locking member 5 to couple the movable body 3 to the static body 2.

The locking member 5 is suitable to integrally couple the bodies 2 and 3 to each other, preventing their mutual rotation.

It is suitable to lock the artificial wrist 1 in one or more activation positions, preferably in the rest position.

The locking member 5 is known per se. It can comprise a locking member provided with a pin and two positions of stable equilibrium, and a spring presser, which can be actuated manually by a suitable lever.

The operation of the artificial wrist 1, previously described in structural terms, is as follows.

Once the artificial wrist 1 is bound to the support (for example a robotic arm, for example a prosthetic arm, or an amputated limb) and to an end effector, such as a robotic hand, it is ready.

Figure 2:
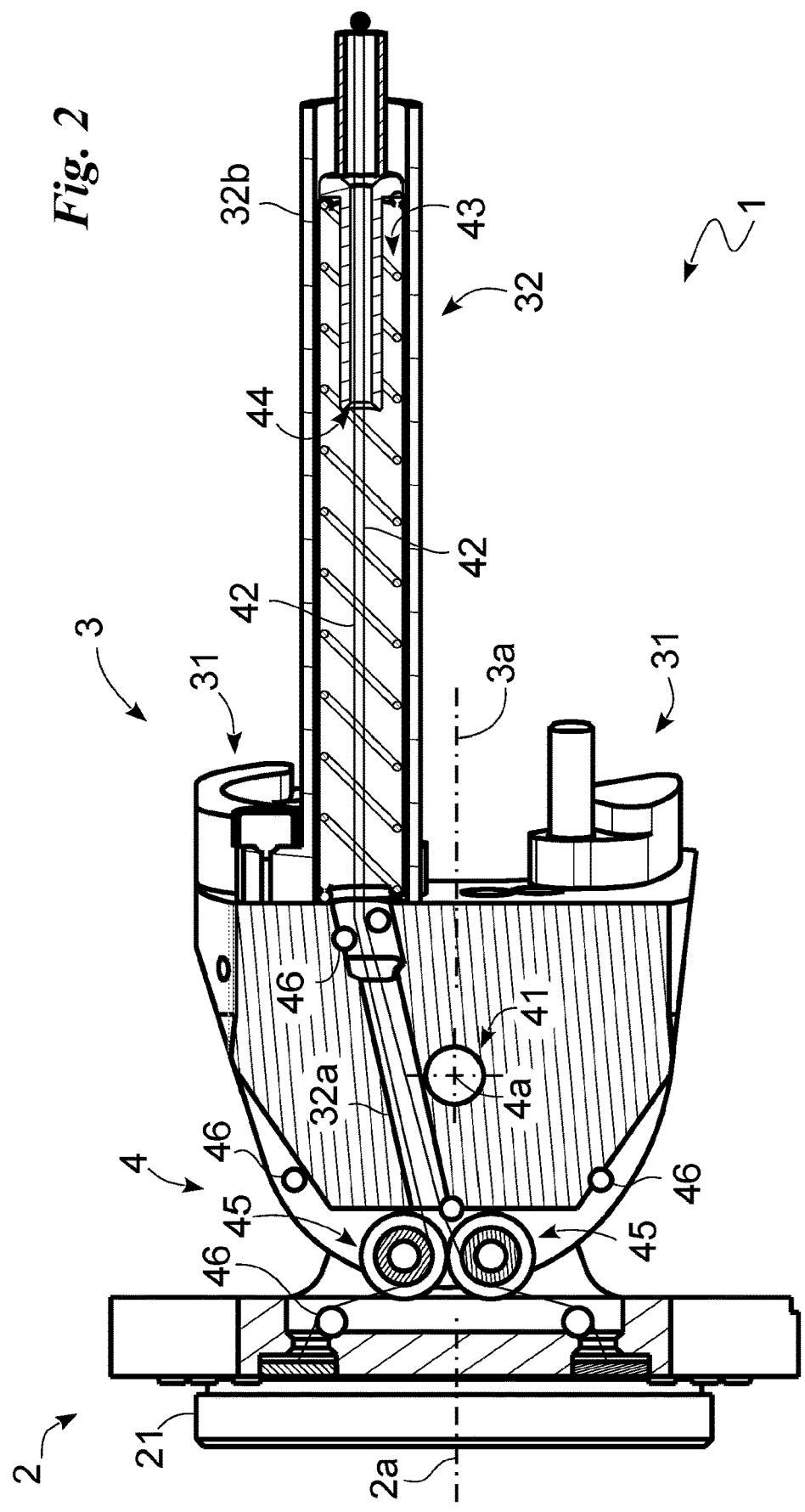
FIG. 2 is a scale representation of a section of FIG. 1.

Initially, the artificial wrist 1 is in the rest position (FIGS. 1 and 2).

When an external force, for example acting on the end effector, creates a torque commanding mutual rotation of the end effector and the support around the axis of rotation 4a, the bodies 2 and 3, i.e. the end effector and the support, mutually rotate with respect to the axis of rotation 4a moving away from the rest position.

This rotation, caused by said external force, between the bodies 2 and 3 causes one of the two cables 42 (for example the first cable) to be tensioned and releases this greater tension on the elastic means 43. The cable 42 thus slides in the channel 32b and causes the elastic means 43 to be compressed (i.e. storage of energy).

The bodies 2 and 3 rotate relative to each other until an activation configuration is reached (FIG. 3) in which the forces created by the cable 42 and the elastic means 43 generate a resulting torque counteracting that given by the external force.

Figure 3:
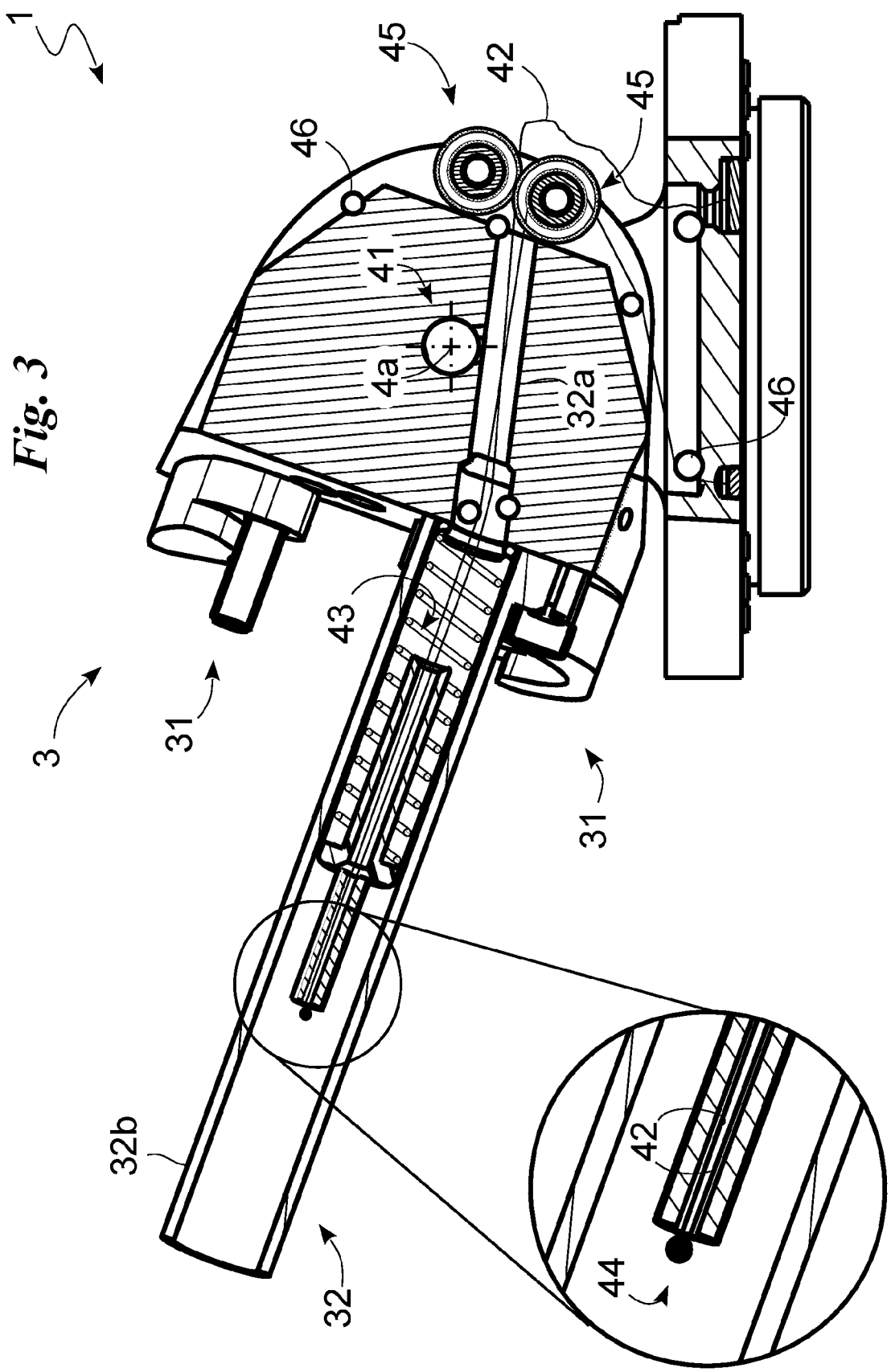
FIG. 3 is a scale representation of the artificial wrist in a different position from that shown in FIGS. 1 and 2.

It should be pointed out that during this rotation in the artificial wrist 1 described herein, representing one of the possible embodiments of the wrist 1 according to the invention, only one of the cables 42 (for example the first cable) is tensioned while the other cable 42 (for example the second cable) is released and, as shown in FIG. 3, can become relaxed.

When the external force is no longer applied, the elastic means 43 releases the stored energy by causing a rotation opposite to the previous one and such as to bring the artificial wrist 1 back to the rest position.

The artificial wrist 1 according to the invention achieves important advantages.

In fact, the artificial wrist 1 has extremely simple mechanics and is therefore easy to manufacture even considering the small dimensions required.

Another advantage is that the artificial wrist 1, compared to known artificial wrists, has limited dimensions and weight, thus resulting in high comfort of use and low manufacturing costs.

These advantages are due to the innovative use of cables 42 and elastic means 43 to control the rotation of the wrist 1, particularly to the particular solution chosen for anchoring the cables 42, and more particularly to the interposition of elastic means 43 between the cable 42 and the movable body 3.

Another advantage is that the artificial wrist 1 allows large rotation angles (up to 140° or even larger depending on the selected configuration of the wrist 1 according to the invention).

For example, the embodiment described above and shown in FIGS. 1-3 has the same rotation angle in both directions (extension and flexion) substantially equal to 70°.

The invention is susceptible of variations falling within the scope of the inventive concept as defined by the claims.

For example the elastic means 43 and the at least one cable 42 may coincide and be identifiable as an elastic cable. Therefore, the junction block 4 may comprise at least one elastic cable, and preferably two elastic cables, one operating in the first direction of rotation, the other in the second direction of rotation.

Another possible alternative may comprise integral connection of the at least one cable 42 to the movable body and interposition of the elastic means 43 between the cable 42 and the static body 2, and in particular the creation of a sliding duct for the elastic means 43 and the cable 42 in the static body 2 instead of in the movable body 3.

In this context, all details are replaceable by equivalent elements, and the materials, shapes and dimensions may be any type of materials, shapes and dimensions.

The invention claimed is:

1. An artificial wrist comprising:
    a static body adapted to be bound to a support;
    a movable body adapted to be bound to an end effector;
    a junction block between said static body and said movable body and defining at least one axis of rotation between said static body and said movable body;
    and wherein said junction block comprises:
    two cables having one end bound in an integral manner to said static body and the other end to said movable body so as to be moved by mutual rotation of said static body and said movable body around said at least one axis of rotation; wherein said two cables being a first cable adapted to be tensioned by mutual rotation of said bodies in a first direction of rotation, and a second cable adapted to be tensioned by mutual rotation of said bodies in a second direction opposite to said first direction of rotation, wherein cables of said junction block are only said first and second cables;
    an elastic means placing said two cables under tensile stress and working in opposition to the movement one of said two cables so as to define a rest position in which said two cables and said elastic means exert a zero resulting torque on said static body and said movable body, and an activation position in which said at least one cable and said elastic means exert a non-zero resulting torque on said static body and said movable body, bringing said static body and said movable body back to said rest position;
    wherein said elastic means is interposed between said movable body and said cables so that the transition into said activation position causes said cables to move, thus loading said elastic means;
    wherein said elastic means having one end integral with said movable body and the other end integral with the said cables;
    wherein said movable body comprises a channel for the passage of said cables; and
    wherein said elastic means is in said channel which guides the sliding of said elastic means.

2. The artificial wrist according to claim 1, wherein said first cable and said second cable are bound to said static body on opposite sides with respect to said at least one axis of rotation.

3. The artificial wrist according to claim 1, wherein said elastic means is a compression spring.

4. The artificial wrist according to claim 3, wherein the end of said compression spring that is integral with said cables are located on the opposite side of said static body with respect to said movable body.

5. The artificial wrist according to claim 1, wherein said two cables are bound to said movable body on the opposite side of said static body.

6. The artificial wrist according to claim 1, wherein said cables and said elastic means coincide and are identifiable as elastic cable.

* * * * *